United States Patent [19]
Thogersen et al.

[11] Patent Number: 5,817,654
[45] Date of Patent: Oct. 6, 1998

[54] N-SUBSTITUTED NAPHTHOFUSED LACTAMS

[75] Inventors: Henning Thogersen, Farum; Birgit Sehested Hansen, Stenlose; Bernd Peschke, Malov; Thomas Kruse Hansen, Herlev; Knud Erik Andersen, Smorum, all of Denmark

[73] Assignee: Novo Nordisk A/S, Bagsvaerd, Denmark

[21] Appl. No.: 790,133

[22] Filed: Jan. 29, 1997

Related U.S. Application Data

[63] Continuation of PCT/DK95/00332, Aug. 17, 1995.

[30] Foreign Application Priority Data

Aug. 17, 1994 [DK] Denmark .................. 0952/94

[51] Int. Cl.⁶ ............... C07D 223/14; C07D 223/16; A61K 31/55
[52] U.S. Cl. .......................... 514/217; 540/522
[58] Field of Search .................. 540/522; 514/217

[56] References Cited

FOREIGN PATENT DOCUMENTS

WO 92/16524  10/1992  WIPO .
WO 94/07486  4/1994  WIPO .

OTHER PUBLICATIONS

Cheng et. al, "Evidence for a Role of Protein Kinase–C in His–D–Tryp–Ala–Trp–D–Phe–Lys–NH2–Induced Growth Hormone Release from Rat Primary Pituitary Cells," Endocrinology, vol. 126, No. 6, pp. 3337–3342, May 20, 1991.

*Primary Examiner*—Mukund J. Shah
*Assistant Examiner*—Ann M. Kessinger
*Attorney, Agent, or Firm*—Steve T. Zelson; Elias J. Lambiris

[57] ABSTRACT

The present invention relates to novel N-substituted naphthofused lactams and salts thereof of the formula

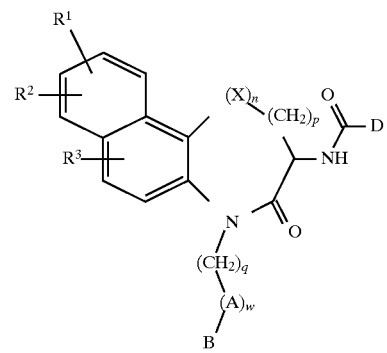

Compounds of the general formula I possess the ability to stimulate the release of endogenous growth hormone. Thus, these compounds may be used in the treatment of conditions which require stimulation of growth hormone production or secretion such as in humans with growth hormone deficiency or where increased growth hormone plasma levels are desired, for instance in elderly patients or in livestock.

15 Claims, No Drawings

N-SUBSTITUTED NAPHTHOFUSED LACTAMS

CROSS-REFERENCE TO RELATED APPLICATIONS

This application is a continuation of application Ser. No. PCT/DK95/00332 filed Aug. 17, 1995 and claims priority under 35 U.S.C. 119 of Danish application Ser. No. 0952/94 filed Aug. 17, 1994, the contents of which are fully incorporated herein by reference.

FIELD OF THE INVENTION

The present invention relates to novel N-substituted naphthofused lactams and salts thereof, to methods for their preparation, to pharmaceutical compositions containing them, the use of these compounds as medicament and to their use for the treatment of medical disorders resulting from a deficiency in growth hormone.

BACKGROUND OF THE INVENTION

Growth hormone is a hormone which stimulates growth of all tissues capable of growing. In addition, growth hormone is known to have a number of effects on metabolic processes, e.g., stimulation of protein synthesis and free fatty acid mobilization and to cause a switch in energy metabolism from carbohydrate to fatty acid metabolism. Consequently, deficiency in growth hormone can result in a number of severe medical disorders, e.g., dwarfism.

Growth hormone is released from the pituitary. The release is under tight control of a number of hormones and neurotransmitters either directly or indirectly. Growth hormone release can be stimulated by growth hormone releasing hormone (GHRH) and inhibited by somatostatin. In both cases the hormones are released from the hypothalamus but their action is mediated primarily via specific receptors located in the pituitary. Also other compounds have been described which stimulate the release of growth hormone from the pituitary. For example arginine, L-3,4-dihydroxyphenylalanine (L-Dopa), glucagon, vasopressin, PACAP (pituitary adenylyl cyclase activating peptide), muscarinic receptor agonists and a synthetic hexapeptide, GHRP (growth hormone releasing peptide) release endogenous growth hormone either by a direct effect on the pituitary or by affecting the release of GHRH and/or somatostatin from the hypothalamus.

In medical disorders where increased levels of growth hormone is desired, the protein nature of growth hormone makes anything but parenteral administration non-feasible. Furthermore, other directly acting secretagogues known so far, e.g., GHRH, GHRP and PACAP, are also longer peptides for which reason oral administration is not feasible. A number of indirectly acting compounds can, however, be administered orally, e.g., L-Dopa and muscarinic receptor agonists although the use of these compounds has been impeded by their induction of side-effects.

DESCRIPTION OF THE INVENTION

The present invention relates to compounds of non-peptidylic nature capable of increasing the release of endogenous growth hormone. These novel compounds can be administered either parenierally, nasally or orally.

In WO 92/16524, WO 94/07483, WO 94/07486, WO 94/05634, U.S. Pat. No. 5,310,737, WO 95/09633, U.S. Pat. No. 5,283,241, GB 2,273,046, U.S. Pat. No. 5,284,841, WO 95/12598, WO 95/03289, U.S. Pat. No. 5,374,721 and WO 95/03290 N-substituted benzofused lactams in which a substituted phenyl or biphenyl group forms part of the N-substituent are claimed to promote the release of growth hormone in humans and animals. Other N-substituted benzofused lactams where different heterocycles are included in the N-substituent are disclosed in WO 94/07486, WO 94/08583 and U.S. Pat. No. 5,284,841. In U.S. Pat. No. 4,228,156 and WO 94/11012 synthetic dipeptides are disclosed and in WO 94/13696 spiro-piperidines connected to benzofused lactams are claimed as growth hormone releasing compounds. The compounds of the present invention differ from the compounds disclosed in the above cited reference in that the lactam is fused to a naphthalene ring.

In addition to the above cited reference, U.S. Pat. Nos. 5,124,328 and 5,077,290 disclose N-substituted-2-heterocyclic morpholine derivatives as animal growth promoters. Further, in U.S. Pat. Nos. 5,030,640, 4,906,645 and 5,019,578 aminoethanol derivatives are disclosed as growth promotors in animals.

The present invention relates to novel N-substituted naphthofused lactams with general formula I

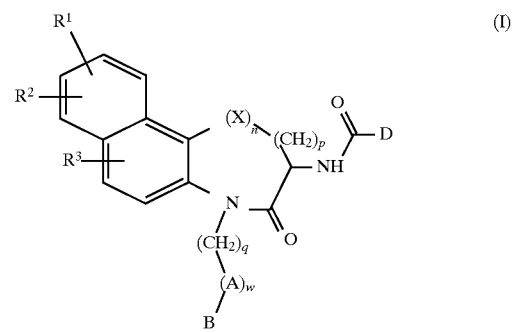

wherein $R^1$, $R^2$ and $R^3$ independently are hydrogen, halogen, trifluoromethyl, $C_{1-6}$-alkyl, $C_{1-6}$-alkoxy or $C_{1-6}$-alkylthio;

n is 0 or 1;

p is 0, 1 or 2;

q is 0, 1, 2, 3 or 4;

w is 0, 1 or 2;

X is —O—, $>S(O)_m$ or $>N—R^4$, wherein $R^4$ is hydrogen or $C_{1-6}$-alkyl; m is 0, 1 or 2;

A is

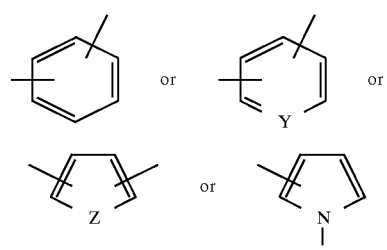

each of which may be substituted with one or more substituents selected from halogen, amino, $C_{1-6}$-alkylamino, $C_{1-6}$-alkyl, $C_{1-6}$-alkoxy or $C_{1-6}$-alkylthio; wherein Y is =N—, and Z is —O—, —S— or $>N—R^5$, wherein $R^5$ is hydrogen or $C_{1-6}$-alkyl;

B is hydrogen or

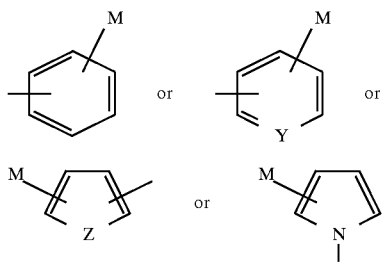

each of which may be substituted with one or more substituents selected from halogen, amino, $C_{1-6}$-alkylamino, $C_{1-6}$-alkyl, $C_{1-6}$-alkoxy or $C_{1-6}$-alkylthio; and wherein Y and Z are as defined above; and M is —$COOR^{12}$, —$CONR^{12}R^{13}$, —$NHCONR^{12}R^{13}$ or —$SO_2NR^{12}R^{13}$, wherein $R^{12}$ and $R^{13}$ independently are hydrogen, $C_{1-6}$-alkyl or $C_{4-8}$-cycloalkyl, or M is any isomer of tetrazole, triazole, oxadiazole and thiadiazole which may be substituted with one or more substituents selected from halogen, amino, $C_{1-6}$-alkylamino, $C_{1-6}$-alkyl, $C_{1-6}$-alkoxy or $C_{1-6}$-alkylthio; D is

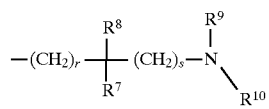

wherein r and s are independently 0, 1, 2 or 3; $R^7$ and $R^8$ are independently hydrogen or $C_{1-10}$-alkyl; or $R^7$ and $R^8$ may be joined together to form alkyl bridges wherein the bridge contains 2–6 carbon atoms; or each of $R^7$ and $R^8$ may independently be joined to one or both of $R^9$ and $R^{10}$ to form alkyl bridges wherein the bridge contains 2–5 carbon atoms; $R^9$ and $R^{10}$ are independently hydrogen, phenyl, substituted phenyl, branched or unbranched $C_{1-10}$-alkyl or branched or unbranched $C_{1-10}$-hydroxylalkyl; or a pharmaceutically acceptable salt thereof.

In all formulas herein n, p, q, w, m, r and s are integers or zero.

The compounds having the general formula I may be prepared by the following method:

Method A:

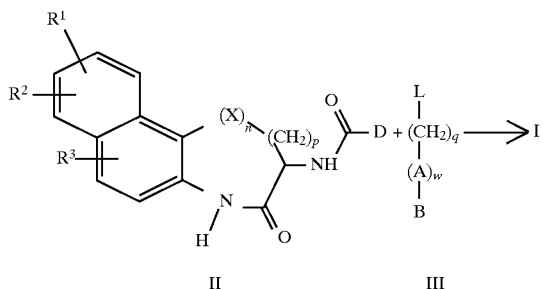

A compound of formula II wherein $R^1$, $R^2$, $R^3$, X, D, n and p are as defined above is allowed to react with a compound of formula III wherein A, B, w and q are as defined above and L is a suitable leaving group such as halogen, p-toluene sulphonate or mesylate. This alkylation reaction may be carried out in a solvent such as e.g. N,N-dimethylformamide or dimethylsulfoxide in the presence of a base e.g. sodium hydride at a temperature up to reflux for the solvent used for e.g. 1 to 120 h.

Compounds of formula II may be prepared by methods similar to those described in WO 92/16524 and compounds of formula III may be prepared by methods familiar to those skilled in the art (e.g. as described in Comprehensive Heterocyclic Chemistry, vol. 5, & 6, Pergamon Press, 1984; Heterocyclic Compounds, vol. 7, Wiley, 1961).

Under certain circumstances it may be necessary to protect the intermediates used in the above methods e.g. a compound of formula II or III with suitable protecting groups. If a primary or secondary amino group is present as in compounds of formula II, this amino group may, for example, be protected by a methoxysulfonyl or a benzyloxycarbonyl group. In compounds of formula III where acidic groups are present, these groups may, for example, be esterified. Furthermore, in compounds of formula III wherein a tetrazole is present, it may, for instance, be tritylated. Introduction and removal of such protecting groups is described in "Protective Groups in Organic Synthesis" T. W. Greene and P. G. M. Wuts 2nd ed. (John Wiley & Sons Inc.).

The compounds of formula I may exist as geometric and optical isomers and all isomers and mixtures thereof are included herein. Isomers may be separated by means of standard methods such as chromatographic techniques or fractional crystallization of suitable salts.

Examples of preferred compounds of formula I are
3-Amino-3-methyl-N-(4-oxo-5-(2'-(tetrazol-5-yl) biphenyl-4-ylmethyl)-2,3,4,5-tetrahydro- 1H-naphtho [2,1-b]azepin-3-yl)butyramide;
3-Amino-3-methyl-N-(4-oxo-5-(4-(4-(5-methyl-[1,3,4] oxadiazol-2-yl)-thien-3-yl)benzyl)-2,3,4,5-tetrahydro-1H-naphtho-[2,1-b]azepin-3-yl)butyramide;
3-((2R)-Hydroxypropylamino)-3-methyl-N-(5-(4-(4-(5-methyl- [1,3,4]oxadiazol-2-yl)thien-3-yl)benzyl)-4-oxo-2,3,4,5-tetrahydro- 1H-naphtho[2,1-b]azepin-3-yl) butyramide;
1-Aminocyclopropanecarboxylic acid (4-oxo-5-[2'-(1H-tetrazole-5-yl)-biphenyl-4-ylmethyl]-2,3,4,5-tetrahydro- 1H-naptho[2,1-b]azepin-3-yl) amide; and
3-Amino-3-methyl-N-(5-benzyl-4-oxo-2, 3,4,5-tetrahydro- 1H-naptho[2,1-b]azepin-3-yl)butyramide.

The compounds according to the invention may optionally exist as pharmaceutically acceptable acid addition salts or esters.

Pharmaceutically acceptable acid addition salts or esters of compounds of formula I include those derived from inorganic or organic acids such as hydrochloric, hydrobromic, sulfuric, acetic, phosphoric, lactic, maleic, phthalic, citric, glutaric, gluconic, methanesulfonic, salicylic, succinic, tartaric, toluenesulfonic, sulfamic and fumaric acid.

It has, surprisingly, been found that compounds of the general formula I have interesting pharmacological properties, and it has been demonstrated that compounds of the general formula I possess the ability to stimulate the release of endogenous growth hormone. Thus, these compounds may be used in the treatment of conditions which require stimulation of growth hormone production or secretion such as in humans with growth hormone deficiency or where increased growth hormone plasma levels are desired, for instance in elderly patients or in livestock.

Growth hormone releasing compounds of formula I are useful in vitro tools for investigating the regulation of growth hormone release.

Compounds of formula I are also useful in vivo tools for evaluating the growth hormone releasing capability of the pituitary. For example, serum samples taken before and after administration of these compounds to humans can be assayed for growth hormone. Comparison of the growth hormone in each serum sample would directly determine the ability of the patients' pituitary to release growth hormone.

Compounds of formula I may be administered to commercially important animals to increase their rate and extent of growth, and to increase milk production.

Accordingly, the present invention further relates to pharmaceutical compositions comprising, as an active ingredient, at least one of the compounds of formula I together with a pharmaceutical carrier or diluent. Optionally, the pharmaceutical composition may comprise at least one compound of formula I combined with one or more compounds exhibiting a different activity, e.g., an antibiotic or other pharmacologically active material.

A further use of growth hormone secretagogue compounds of formula I is in combination with other secretagogues such as GHRP (2 or 6), GHRH and its analogues, growth hormone and its analogues or somatomedins including IGF-1 and IGF-2.

To those skilled in the art, it is well known that the current and potential uses of growth hormone in humans are varied and multitudinous. Thus, compounds of formula I can be administered for purposes of stimulating release of growth hormone from the pituitary and would then have similar effects or uses as growth hormone itself. The uses of growth hormone may be summarized as follows: stimulation of growth hormone release in the elderly; prevention of catabolic side effects of glucocorticoids, treatment of osteoporosis, stimulation of the immune system, treatment of retardation, acceleration of wound healing, accelerating bone fracture repair, treatment of growth retardation, treating renal failure or insufficiency resulting from growth retardation, treatment of physiological short stature including growth hormone deficient children and short stature associated with chronic illness, treatment of obesity and growth retardation associated with obesity, treating growth retardation associated with the Prader-Willi syndrome and Turner's syndrome; accelerating the recovery and reducing hospitalization of burn patients; treatment of intrauterine growth retardation, skeletal dysplisia, hypercortisolism and Cushing's syndrome; induction of pulsatile growth hormone release; replacement of growth hormone in stressed patients, treatment of osteochondrodysplasias, Noonan's syndrome, schizophrenia, depressions, Alzheimer's disease, delayed wound healing and psychosocial deprivation, treatment of pulmonary dysfunction and ventilator dependency, attenuation of protein catabolic responses after major surgery, reducing cachexia and protein loss due to chronic illness such as cancer or AIDS; treatment of hyperinsulinemia including nesidioblastosis, adjuvant treatment for ovulation induction; to stimulate thymic development and prevent the age-related decline of thymic function, treatment of immunosuppressed patients, improvement in muscle strength, mobility, maintenance of skin thickness, metabolic homeostasis, renal hemeostasis in the frail elderly, stimulation of osteoblasts, bone remodelling and cartilage growth, stimulation of the immune system in companion animals and treatment of disorder of aging in companion animals, growth promotant in livestock and stimulation of wool growth in sheep.

PHARMACOLOGICAL METHODS

Compounds of formula I were evaluated in vitro for their efficacy and potency to release growth hormone in primary rat somatotrophs.

Rat primary somatotrophs were prepared essentially as described previously (Chen et al., Endocrinology 1991, 129, 3337–3342 and Chen et al., Endocrinology 1989, 124, 2791–2798). Briefly, rats were killed by decapitation. The pituitary was quickly removed. The pituitaries were digested with 0.2 % collagenase n 0.2% hyaluronidase in Hanks balanced salt solution. The cells were resuspended in Dulbecco's modified eagles medium containing 0.37% $NaHCO_3$, 10% horse serum, 2.5% fetal calf serum, 1% nonessential amino acids, 1% glutamire and 1% pen/strep and adjusted to 1.5 ×$10^5$ cells/ml. One ml of this suspension was placed in each well of 24-well trays and left for 2–3 days before release experiments were performed.

On the day of the experiments, cells were washed twice with the above medium containing 25 mM HEPES, pH 7.4. Growth hormone release were initiated by addition of medium containing 25 mM HEPES and test compound. Incubation was carried out for 15 minutes at 37° C. After incubation growth hormone released to the medium was measured by a standard RIA assay.

Compounds of formula I were evaluated for their in vivo effects on growth hormone release in pentobarbital anaesthetized female rats as described previously (Bercu et al. Endocrinology 1991, 129, 2592–2598). Briefly, adult male Sprague-Dawley rats were anesthetized with pentobarbital 70 mg/kg ip. After full anaesthesia was obtained the rats were implanted with a trachea cannula and catheters in the carotid artery and the jugular vein. After a 15 minute recovery, a blood sample was taken at time 0. The pituitary secretagogues were administered i.v. and artery blood samples were put on ice for 15 minutes and then centrifuged for 2 minutes at 12,000 x g. The serum was decanted and amount of GH determined using a standard RIA assay.

For the above indications the dosage will vary depending on the compound of formula I employed, on the mode of administration and on the therapy desired. However, generally dose levels between 0.0001 and 100 mg/kg body weight daily are administered to patients and animals to obtain effective release of endogenous growth hormone. Usually, dosage forms suitable for oral administration comprise from about 0.0001 mg to about 500 mg preferably from about 0.001 mg to about 100 mg of the compounds of formula I admixed with a pharmaceutical carrier or diluent.

The compounds of formula I may be administered in pharmaceutically acceptable acid addition salt form or, where appropriate, as an alkali metal or alkaline earth metal or lower alkylammonium salt. Such salt forms exhibit approximately the same order of activity as the free base forms.

Pharmaceutical compositions containing a compound of the present invention may be prepared by conventional techniques and appear in conventional forms, for example capsules, tablets, solutions or suspensions.

The pharmaceutical carrier employed may be a conventional solid or liquid carrier. Examples of solid carriers ire lactose, terra alba, sucrose, talc, gelatin, agar, pectin, acacia, magnesium stearate and stearic acid. Examples of liquid carriers are syrup, peanut oil, olive oil and water.

Similarly, the carrier or diluent may include any sustained release material known in the art, such as glyceryl monostearate or glyceryl distearate, alone or mixed with a wax.

If a solid carrier is used for oral administration, the preparation can be tabletted, placed in a hard gelatin capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatin capsule or sterile injectable liquid such as an aqueous or non-aqueous liquid suspension or solution.

Generally, the compounds of the present invention are dispensed in unit dosage form comprising 50–200 mg of active ingredient in or together with a pharmaceutically acceptable carrier per unit dosage.

The dosage of the compounds according to this invention is suitably 1–500 mg/day, e.g. about 100 mg per dose, when administered to patients, e.g. humans, as a medicament.

A typical tablet which may be prepared by conventional tabletting techniques may contain:

| Core: | |
|---|---|
| Active compound (as free compound or salt thereof) | 100 mg |
| Colloidal silicon dioxide (Areosil ®) | 1.5 mg |
| Cellulose, microcryst. (Avicel ®) | 70 mg |
| Modified cellulose gum (Ac-Di-Sol ®) | 7.5 mg |
| Magnesium stearate | |
| Coating: | |
| HPMC | approx. 9 mg |
| *Mywacett ® 9-40 T | approx. 0.9 mg |

*Acylated monoglyceride used as plasticizer for film coating.

The route of administration may be any route which effectively transports the active compound to the appropriate or desired site of action, such as oral, transdermal, nasal, pulmonary or parenteral, the oral route being preferred.

EXAMPLES

The process for preparing compounds of formula I and preparations containing them is further illustrated in the following examples, which, however, are not to be construed as limiting.

The structures of the compounds are confirmed by either elemental analysis or NMR. NMR shifts ($\delta$) are given in parts per million (ppm). mp is melting point and is given in ° C. Column chromatography was carried out using the technique described by W. C. Still et al, J. Org. Chem. 1978, 43, 2923–2925 on Merck silica gel 60 (Art. 9385). Compounds used as starting materials are either known compounds or compounds which can readily be prepared by methods known per se.

Abbreviations:
TLC: thinlayer chromatography
TFA: trifluoroacetic acid
DMSO: dimethylsulfoxide
DMF: N,N-dimethylformamide
EDAC: 1-ethyl-3-(3-dimethylaminopropyl)carbodiimide-hydrochloride
HOAt: hydroxyazabenzotriazole
HOBt: hydroxybenzotriazole
THF: tetrahydrofuran
AIBN: azoisobutyronitrile
NBS: N-bromosuccinimide HPLC-analysis:
Method A.

The RP-HPLC analysis was performed using UV detection at 214 nm and a Vydac 218TP54 4.6 mm ×250 mm 5 $\mu$ C-18 silica column (The Separations Group, Hesperia) which was eluted at 1 ml/minute at 42° C. The column was equilibrated with 5% $CH_3CN$ in a buffer consisting of 0.1 M $(NH_4)_2SO_4$, which was adjusted to pH 2.5 with 4 M $H_2SO4$ and eluted by a gradient of 5% to 60% $CH_3CN$ in the same buffer during 50 minutes.

Method B.

With the same column as in method A elution was performed using a gradient of 0% $CH_3CN$ / 0.1% TFA / $H_2O$ to 90% $CH_3CN$ / 0.1% TFA / H2O during 50 minutes.

Method C.

A 5 $\mu$m C-18 4×250 mm column eluting with a 20–80% gradient of 0.1% TFA/acetonitrile and 0.1% TFA/water over 25 minutes and T=35° C.

EXAMPLE 1

3-Amino-3-methyl-N-(4-oxo-5-(2'-(tetrazol-5-yl) biphenyl-4-ylmethyl)-2,3,4,5-tetrahydro- 1H-naphtho[2,1-b]azepin-3-yl)butyramide trifluoroacetate.

3,4-Dihydro-2H-phenanthren-1-one-oxime.

To a solution of sodium acetate trihydrate (7.07 g, 52 mmol) in water (30 ml) was added hydroxylamine hydrochloride (3.61 g, 52 mmol). Ethanol (75 ml) and 3,4-dihydro-2H-phenantren-1-one (5.0 g, 26 mmol) were added and the suspension was heated at reflux for 2h. The reaction mixture was cooled on an ice-bath and the precipitated solid was isolated by filtration, washed with cold water and dried in vacuo to afford 4.8 g of 3,4-dihydro-2H-phenanthren-1-one-oxime.

mp: 174–175° C.

$^1$H NMR ($CDCl_3$) $\delta$ 2.05 (p, 2H, J=8Hz); 2.91 (t, 2H, J =8Hz); 3.20 (t, 2H, J =8Hz); 7.52 (m, 2H); 7.67 (d, 1H, J=9Hz); 7.82 (d, 1H, J=9Hz); 8.05 (t,2H, J=9Hz); 8.22 (brs, 1H).

4-Oxo-2,3,4,5-tetrahydro-1H-naphtho[2,1-b]azepine.

A solution of methanesulfonic acid (25 ml) and phosphorus pentaoxide (5.2 g, 37 mmol) was heated at 90° C. for 3.5 h. The solution was cooled to 50° C. and 3,4-dihydro-2H-phenanthren-1-one-oxime (4.8 g, 23 mmol) was added. The solution was heated at 60° C. for 10 minutes and then at 80° C. for 3.5 hr. The hot reaction mixture was added to a mixture of ice (300 g) and water (100 ml). The precipitated solid was isolated by filtration, redissolved in dichloromethane (50 ml), dried ($MgSO_4$) and evaporated in vacuo to afford a white product. Purification was achieved using column chromatography with silica gel (200 g) and a mixture of heptane and ethyl acetate (1:2) to afford 4.8 g of 4-oxo-2,3,4,5-tetrahydro-1H-naphtho[2,1-b]azepine.

mp: 186°–187° C.

$^1$H NMR ($CDCl_3$) $\delta$ 2.16 (t,2H, J=8Hz); 2.21–2.30 (m, 2H); 3.14 (t,2H, J=8Hz); 7.19 (d, 1H, J=9Hz); 7.46 (t, 1H, J=9Hz); 7.55 (t, 1H, J=9Hz); 7.80 (d, 1H, J=9Hz); 7.90(d, 1H, J=9Hz); 8.13 (d, 1H, J=9Hz); 9.71 (s, 1H).

3,3-Dichloro-4-oxo-2,3,4,5-tetrahydro- 1 H-naphtho[2,1-b] azepine.

To a suspension of 4-oxo-2,3,4,5-tetrahydro-1H-naphtho [2,1-b]azepine (4.8 g, 23 mmol) in toluene (125 ml) was added phosphorus pentachloride (14.2 g, 68 mmol) and the reaction mixture was heated at 90° C. for 1 h. After cooling to room temperature the solvent was evaporated in vacuo and the residue was suspended in glacial acetic acid (50 ml). The suspension was heated at 70° C. for 0.5 h and cooled to 8° C. Water (100 ml) and ice (100 g) were added and the precipitated solid was isolated by filtration, washed with water and dried in vacuo. This afforded 6.3 g of 3,3-dichloro-4-oxo-2,3,4,5-tetrahydro-1H-naphtho [2,1-b] azepine.

mp: 187°–191° C.

$^1$N NMR ($CDCl_3$) $\delta$ 6 3.36 (t, 2H, J=9Hz); 3. 45(t, 2H, J=9Hz); 7.14(d, 1H, J=9Hz); 7.50 (t, 1H, J=9Hz); 7.59 (t, 1H, J=9Hz); 7.77 (d, 1H, J=9Hz); 7.85 (d, 1H, J=9Hz); 7.91 (brs,1H); 8.0 (d, 1H, J=9Hz).

3-Chloro-4-oxo-2,3,4,5-tetrahydro- 1H-naphtho[2,1-b]azepine.

A solution of 3,3-dichloro-4-oxo-2,3,4,5-tetrahydro-1H-naphtho[2,1-b]azepine (6.2 g, 22 mmol) in glacial acetic acid (200 ml) was placed under an atmosphere of nitrogen. Sodium acetate trihydrate (3.8 g, 28 mmol) was added. After 5 minutes palladium on carbon (10%, 0.6 g) was added and the reaction mixture was hydrogenated at atmospheric pressure and room temperature using 450 ml of hydrogen gas. The reaction mixture was filtered through Celite and the solvent was evaporated in vacuo. After reevaporation with toluene (250 ml), the residue was suspended in water (100 ml), stirred for 5 minutes and the solid was isolated by filtration and dried in vacuo to afford 1.7 g of 3-chloro-4-oxo-2,3,4,5-tetrahydro-1H-naphtho[2,1-b]azepine.

$^1$H NMR (CDCl$_3$) δ 2.64–2.74 (m, 1H); 2.85–2.95 (m, 1H); 3.09–3.18 (m, 1H); 3.50–3.55 (m, 1H); 4.49 (dd, 1H); 7.15 (d, 1H, J=9Hz); 7.50 (t, 1H, J=9Hz); 7.60 (t, 1H, J=9Hz); 7.78 (d, 1H, J=9Hz); 7.80 (brs, 1H); 7.87 (d, 1H, J=9Hz); 8.04 (d,1H, J=9Hz).

3-Azido-4-oxo-2,3,4,5-tetrahydro- 1H-naphtho[2,1-b]azepine.

To a suspension of sodium azide (0.55 g, 8.4 mmol) in DMSO (17 ml) was added 3-chloro-4-oxo-2,3,4,5-tetrahydro-1H-naphtho[2,1-b]azepine (1.6 g, 6.7 mmol) and the suspension was heated at 80° C. for 2.5 h. The hot reaction mixture was added on ice (30 g) and the precipitate was filtered and purified by chromatography on silica gel (200 g) using initially heptane as eluent and subsequently a mixture of heptane and ethyl acetate (1:1) to afford 1.1 g of 3-azido-4-oxo-2,3,4,5-tetrahydro-1H-naphtho[2,1-b]azepine.

mp: 190–192° C.

1H NMR (CDCl$_3$) δ 2.44–2.53 (m, 1H); 2.64–2.75 (m, 1H); 3.04–3.14 (m, 1H); 3.53–3.60 (m, 1H); 3.89 (dd, 1H); 7.15 (d, 1H, J=9Hz); 7.50 (t, 1H, J=9Hz); 7.60 (t, 1H, J=9Hz); 7.78 (d, 1H, J=9Hz); 7.83 (brs,1H); 7,87 (d, 1H, J=9Hz); 8.04 (d, 1h, J=9Hz).

3-Amino-4-oxo-2,3,4,5-tetrahydro-1H-naphtho [2,1-b] azepine.

A solution of 3-azido-4-oxo-2,3,4,5-tetrahydro-1H-naphtho[2, 1-b]azepine (1.0 g, 4.0 mmol) in dry THF (20 ml) was placed under an atmosphere of nitrogen and cooled by an ice-bath. A solution of sodium borohydride (0.17 g, 4.4 mmol) in ethanol (20 ml) was added dropwise during a period of 10 minutes and the reaction mixture was heated at reflux temperature for 20 h. The volatiles were evaporated in vacuo and the residue was purified by columm chromatography on silica gel (200 g) using dichloromethane and a mixture of ethanol and 25% NH$_3$(aq) (9:1) (gradient 0% to 10%) as eluent. This afforded 0.30 g of 3-amino-4-oxo-2,3,4,5-tetrahydro-1H-naphtho [2,1-b]azepine.

1H NMR (CDCl$_3$) δ 2.05–2.15 (m, 1H); 2.64–2.75 (m, 1H); 2.95–3.05 (m, 1H); 3.44 (dd, 1H); 3.48–3.52 (m, 1H); 7.13 (d, 1H, J=9Hz); 7.49 (t, 1H, J=9Hz); 7.56 (t, 1H, J=9Hz); 7.60 (brs, 1H); 7.75 (d, 1H, J=9Hz); 7.85 (d, 1H, J=9Hz); 8.07 (d, 1H, J=9Hz).

(1, 1-Dimethyl-2-(4-oxo-2,3,4,5-tetrahydro-1H-naphtho[2,1-b]azepin-3-ylcarbamoyl)ethyl)carbamic acid tert-butyl ester.

To a solution of 3-tert-butyloxycarbonylamino-3-methylbutanoic acid (0.26 g, 1.2 mmol) in DMF (15 ml) was added EDAC (0.24 g, 1.2 mmol). After 15 minutes at room temperature,3-amino-4-oxo-2,3,4,5-tetrahydro-1H-naphtho [2,1-b]azepine (0.25 g,1.1 mmol) was added and the reaction mixture was stirred for 6 h. Water (80 ml) was added and the solution was extracted with ethyl acetate (30 ml). The organic phase was washed with sodium bicarbonate (20 ml), water (20 ml) and dried (MgSO$_4$). The solvent was evaporated in vacuo and the residue was purified by column chromatography on silica gel (50 g) using heptane and ethyl acetate (1:3) as eluent. This afforded 0.49 g of (1,1-dimethyl-2-(4-oxo-2,3,4,5-tetrahydro- 1H-naphtho[2,1-b] azepin-3-ylcarbamoyl)ethyl)carbamic acid tert-butyl ester.

(1,1-Dirnethyl-2-(4-oxo-5-(2'-(N-triphenylmethyltetrazol-5-yl)biphenyl-4-ylmethyl)-2,3,4,5-tetrahydro-1H-naphtho [2,1-b]azepin-3-ylcarbamoyl)ethyl)carbamic acid tert-butyl ester.

A solution of dry powdered potassium hydroxide (0.23 g, 4.0 mmol) and (1,1-dimethyl-2-(4-oxo-2,3,4,5-tetrahydro-1H-naphtho[2,1-b]azepin-3-ylcarbamoyl)ethyl)carbamic acid tert-butyl ester (0.49 g, 1.0 mmol) in DMSO (15 ml) was stirred for 0.5 h under an atmosphere of nitrogen. 5-(4'-Bromomethyl-biphenyl-2-yl)-N-(triphenylmethyl) tetrazole (0.59 g, 1.1 mmol) was added and the mixture was stirred for 1 h. A 10% aqueous solution of ammoniumchloride (30 ml), water (100 ml) and ethyl acetate (60 ml) were added and the phases were separated. The organic layer was dried (MgSO$_4$), and the solvent was evaporated in vacuo. Purification by columm chromatography on silica gel (100 g) using heptane and ethyl acetate (2:3) as eluent afforded 0.45 g of (1, 1-dimethyl-2-(4-oxo-5-(2'-(N-triphenylmethyltetrazol-5-yl)biphenyl-4-ylmethyl)-2,3,4,5-tetrahydro-1H-naphtho[2,1-b]azepin-3-ylcarbamoyl)ethyl)- carbamic acid tert-butyl ester.

$^1$H NMR (CDCl$_3$) δ 1.26 (s, 2H); 1.34 (s, 6H); 1.42 (s, 9H); 2.46 (dd, 2H); 3.16 (dd, 1H); 4.45 (m, 1H); 4.74 (d, 1H); 5.26 (s, 1H); 5.31 (s, 1H); 6.70 (d, 1H); 6.93 (d, 1H); 7.00 (s, 4H); 7.21–7.35 (m, 8H); 7.39–7.53 (m, 5H); 7.71(d, 1H); 7.80–7.92 (m, 3H)

To a solution of (1,1-dimethyl-2-(4-oxo-5-(2'-(N-triphenylmethyl-1H-tetrazol-5-yl)biphenyl-4-ylmethyl)-2,3, 4,5-tetrahydronaphtho[2,1-b]azepin-3-ylcarbamoyl)ethyl) carbamic acid tert-butyl ester (0.45 g, 0.67 mmol) in dichloromethane (20 ml) was added trifluoroacetic acid (2 ml). The reaction mixture was stirred for 4.5 h and water (5 ml) was added. The solvent was evaporated in vacuo and the residue was purified by column chromatography (Waters RP18 silica 75 μ, 40 g) using methanol, water and TFA (60:40:0.5) as eluent. The solvent was evaporated in vacuo and the residue was redissolved in methanol (30 ml) and evaporated in vacuo to afford 0.31 g of the title compound.

$^1$H NMR (d$_6$-DMSO) δ 1.19 (s, 3H); 1.25 (s, 3H); 2.13–2.46 (m, 3H); 2.40 (s, 1H); 2.41 (s, 1H); 3.40 (dd, 1H); 4.20–4.28 (m, 1H); 4.90 (d, 1H); 5.33( d, 1H); 6.98 (d, 2H); 7.16 (d, 2H); 7.47–7.67 (m, 8H); 7.75 (brs, 2H); 7.89–7.98 (m, 2H); 8.14 (d, 1H); 8.69 (d, 1H).

HPLC: R$_t$=30.5 minutes (Method A)

Calculated for C$_{33}$H$_{33}$N$_6$O$_2$, 1½ TFA, 1½H$_2$O:

C, 57.23%; H, 4.99%; N, 12.98%; Found:

C, 57.35%; H, 4.81%; N, 12.60%.

EXAMPLE 2

3-Amino-3-methyl-N-(4-oxo-5-(4-(4-(5-methyl-[1,3, 4]oxadiazol-2-yl)thien-3-yl)benzyl)-2,3,4,5-tetrahydro-1H-naphtho[2,1-b] azepin-3-yl) butyramide.

3,3-Dichloro-4-oxo-2,3,4,5-tetrahydro-1H-naphtho[2,1-b]azepine.

To a suspension of 4-oxo-2,3,4,5-tetrahydro-1H-naphtho [2,1-b]azepine (24.1 g, 114 mmol, prepared in a maimer similar to that in example 1) in toluene (750 ml) was added phosphorus pentachloride (71.3 g, 342 mmol). The reaction mixture was slowly heated to 90° C. and then heated at 90° C. for 1 h. Activated charcoal was added and the mixture was allowed to cool to ambient temperature. The mixture was filtered and the filtrate was evaporated in vacuo. The oily residue was dissolved in glacial acetic acid (300 ml), heated at 70° C. for 30 minutes and cooled to 10° C. Water (1200 ml) was added and stirring on an ice bath was continued for 15 minutes. The precipitated solid was isolated by filtration, washed with water and dried in vacuo. This afforded 28.5 g of 3,3-dichloro-4-oxo-2,3,4,5-tetrahydro-1H-naphtho[2,1-b]azepine as a solid.

$^1$H NMR (CDCl$_3$) δ 3.36 (dt, 2H); 3.45(dt, 2H); 7.15 (d, 1H); 7.48 (t, 1H); 7.58 (t, 1H); 7.75 (d, 1H); 7.86 (d, 1H); 8.00 (d, 1H); 8.08 (brs, 1H).

3-Chloro-4-oxo-2,3,4,5-tetrahydro- 1H-naphtho[2,1-b] azepine.

A solution of 3,3-dichloro-4-oxo-2,3,4,5-tetrahydro-1H-naphtho- [2,1-b]azepine (28.0 g, 100 mmol) in glacial acetic acid (250 ml) was placed under an atmosphere of nitrogen. Sodium acetate (22.6 g, 275 mmol), sodium hypophosphite hydrate (24.6 g, 280 mmol) and palladium on carbon (10%, 1.5 g) were added. The reaction mixture was stirred at 56° C. for 20 h under an atmosphere of nitrogen. The mixture was allowed to cool to ambient temperature and then filtered. The solid was boiled with THF (3×700 ml) and filtered while still warm. The combined THF phases were evaporated in vacuo to give 19.1 g of 3-chloro-4-oxo-2,3,4,5-tetrahydro-1H-naphtho-[2,1-b]azepine.

$^1$H NMR (CDCl$_3$) δ 2.65–2.73 (m, 1H); 2.85–2.95 (m, 1H); 3.11–3.19 (m, 1H); 3.50–3.56 (m, 1H); 4.49 (dd, 1H); 7.18 (d, 1H); 7.50 (t, 1H); 7.60 (t, 1H); 7.78 (d, 1H); 7.88 (d, 1H); 8.01 (brs, 1H); 8.04 (d, 1H).

3-Azido-4-oxo-2,3,4,5-tetrahydro-1H-naphtho[2,1-b] azepine.

To a suspension of 3-chloro-4-oxo-2,3,4,5-tetrahydro-1H-naphtho-[2,1-b]azepine (16.6 g, 67.6 mmol) in DMSO (80 ml) was added sodium azide (8.8 g, 135 mmol) and the suspension was heated at 60° C. for 5 h. The hot reaction mixture was poured into water (1 L). The precipitate was isolated by filtration and washed with water. After drying in vacuo 16.3 g of 3-azido-4-oxo-2,3,4,5-tetrahydro-1H-naphtho[2,1-b]azepine was obtained.

1H NMR (CDCl$_3$) δ 2.44–2.53 (m, 1H); 2.62–2.75 (m, 1H); 3.06–3.13 (m, 1H); 3.58 (dd, 1H); 3.90 (dd, 1H); 7.18 (d, 1H); 7.52 (t, 1H); 7.60 (t, 1H); 7.80 (d, 1H); 7.87 (d, 1H); 8.00 (brs, 1H); 8.06 (d, 1H).

3-Amino-4-oxo-2,3,4,5-tetrahydro-1H-naphtho[2,1-b] azepine

To a solution of 3-azido-4-oxo-2,3,4,5-tetrahydro-1H-naphtho-[2,1-b]azepine (16.0 g, 63.4 mmol) in a mixture of dry dioxane (150 ml) and ethanol (150 ml), palladium on carbon (10%, 2 g) was added. This mixture was hydrogenated under a pressure of 5 bar and with efficient stirring for 24 h. The reaction mixture was filtered and excess hydrogenchloride in ethanol was added. The precipitated solid was isolated, washed with ethanol and dried to give 14.4 g of 3-amino-4-oxo-2,3,4,5-tetrahydro-1H-naphtho[2,1-b] azepine hydrochloride. The above hydrochloride (14.2 g) was dissolved into water (800 ml) by warming. A 25% aqueous ammonia solution was added and a precipitate was formed. The solid was isolated by filtration, washed with water and dried in vacuo to give 11.9 g of 3-amino-4-oxo-2,3,4,5-tetrahydro-1H-naphtho[2,1-b]azepine.

$^1$H NMR (CDCl$_3$) δ 2.05–2.15 (m, 1H); 2.65–2.75 (m, 1H); 2.95–3.05 (m, 1H); 3.45 (dd, 1H); 3.50 (dd, 1H); 7.15 (d, 1H); 7.50 (t, 1H); 7.58 (t, 1H); 7.75 (d, 1H); 7.79 (brs, 1H); 7.86 (d, 1H); 8.08 (d, 1H).

3-Amino-4-oxo-2,3,4,5-tetrahydro-1H-naphtho[2,1-b] azepine (4.5 g) was dissolved in hot ethanol (250 ml) and L(+)-tartaric acid dissolved in hot ethanol (50 ml) was added at 70° C. The resulting suspension was allowed to cool to ambient temperature with stirring. The solid was isolated by filtration and washed with ethanol. Then it was dissolved into boiling water (250 ml) treated with activated charcoal and filtered hot. The filtrate was allowed to cool to ambient temperature with stirring and then stirred 3h at room temperature. The solid was isolated by filtration and dried to give 3.3 g which was dissolved into hot water (200 ml). At 40°–50° C. excess of a 25% solution of aqueous ammonia was added and the solid was isolated by filtration. This afforded after drying 2.1 g of unresolved 3 -amino-4-oxo-2,3,4,5 -tetrahydro-1H-naphtho [2,1-b]azepine.

(1,1-Dimethyl-2-(4-oxo-2, 3, 4, 5 -tetrahydro-1H-naphtho [2, 1 -b]azepin-3-ylcarbamoyl)ethyl)carbamic acid tert-butyl ester.

A solution of 3-tert-butyloxycarbonylamino-3-methylbutanoic acid (2.43 g, 11.2 mmol) and 1-hydroxybenzotriazole (1.52 g, 11.3 mmol) in DMF (30 ml) was placed under an atmosphere of nitrogen. EDAC (2.19 g, 11.4 mmol) was added and the reaction mixture was stirred for 10 minutes at room temperature. Unresolved 3-amino-4-oxo-2,3,4,5-tetrahydro-1H-naphtho[2,1-b]-azepine (2.3 g, 10.2 mmol) was added and the reaction mixture was stirred overnight at room temperature. The reaction mixture was poured into water (200 ml) and the solution was extracted with dichloromethane (2×250 ml). The combined organic extracts were washed with 10% sodium bicarbonate (2×150 ml) and dried (MgSO$_4$). The solvent was evaporated in vacuo to give a solid residue which was suspended in diethyl ether. Filtration and drying afforded 4.5 g of (1,1-dimethyl -2-(4-oxo-2,3,4,5-tetrahydro-1H-naphtho[2,1-b]azepin-3-ylcarbamoyl)ethyl) carbamic acid tert-butyl ester.

$^1$H NMR (CDCl$_3$) δ 1.35 (s, 6H); 1.43 (s, 9H); 2.05–2.13 (m, 1H); 2.45–2.60 (m, 2H); 2.90-3.08 (m, 2H); 3.50 (dd, 1H); 4.50–4.56 (m, 1H); 5.22 (brs, 1H); 6.75 (d, 1H); 7.12 (d, 1H); 7.49 (t, 1H); 7.57 (t, 1H); 7.73 (d, 1H); 7.85 (d, 1H); 7.88 (brs, 1H); 8.03 (d, 1H).

5-Methyl-2-(4-(4-methylphenyl)-3-thienyl)-[1,3,4] oxadiazole

A mixture of 5-(4-(4-methylphenyl)-3-thienyl)-tetrazole (3.3 g, 13.2 mmol) and acetic anhydride (50 ml) was heated at reflux temperature for 1 h. The resulting solution was evaporated in vacuo to give an oily residue which was dissolved into ethyl acetate (100 ml). The organic solution was vashed with a sodium bicarbonate solution (100 ml), treated with activated charcoal and dried (MgSO$_4$). Filtration and evaporation in vacuo afforded 3.4 g of 5-methyl-2-(4-(4-methylphenyl)-3-thienyl)-[1,3,4]- oxadiazole as an oil.

$^1$H NMR (CDCl$_3$) δ 2.38 (s, 3H); 2.45 (s, 3H); 7.18 (d, 2H); 7.25 (d, 2H); 7.29 (d, 1H); 8.03 (d, 1H).

5-Methyl-2-(4-(4-bromome thylphenyl)-3-thienyl)-[1,3,4] oxadiazole

5-Methyl-2-(4-(4-methylphenyl)-3-thienyl)-[1,3,4] oxadiazole (3.4 g, 13.3 mmol) was dissolved into carbon-tetrachloride (60 ml). AIBN (0.21 g), sodium acetate (0.52 g), NBS (2.6 g, 14.6 mmol) and glacial acetic acid (0.52 ml) were added. The reaction mixture was heated at reflux temperature for 8h and then allowed to cool to ambient temperature. The reaction mixture was filtered through silica gel and the filtrate was evaporated in vacuo. The oily residue was dried in vacuo over sodium hydroxide to give 2.6 g of crude 5-methyl-2-(4-(4-bromomethylphenyl)-3-thienyl)-[1,3,4]oxadiazole.

¹H NMR (CDCl₃) δ 2.47 (s, 3H); 4.55 (s, 2H); 7.32–7.35 (m, 3H); 7.40 (d, 2H); 8.08 (d, 1H). (1,1-Dimethyl-2-(4-oxo-5-(4-(4-(5-methyl-[1,3,4]oxadiazol-2-yl)-3-thienyl)benzyl)-2,3,4,5-tetrahydro-1H-naphtho[2,1-b]azepin-3-ylcarbamoyl)ethyl)carbamic acid tert-butyl ester.

A solution of powdered potassium hydroxide (2.0 g, 29.8 mmol) and (1, 1-dimethyl-2-(4-oxo-2,3,4,5-tetrahydro-1H-naphtho -[2,1-b]azepin-3-ylcarbamoyl)ethyl)carbamic acid tert-butylester (3.2 g, 7.46 mmol) in DMSO (30 ml) was stirred for 30 minutes under an atmosphere of nitrogen. A solution of 5-methyl -2-(4-(4-bromomethylphenyl)-3-thienyl)-[1,3,4]oxadiazole (2.5 g, 7.46 mmol) in DMSO (10 ml) was added and the reaction mixture was stirred for 1 h at ambient temperature. The mixture was poured into water (500 ml) and extracted with dichloromethane (600 ml). The organic extract was washed with water (100 ml), a 5% tartaric acid solution (200 ml), brine and dried (MgSO₄). Evaporation in vacuo afforded a residue which was purified by columm chromatography on silica gel (200 g) using ethyl acetate as eluent. This afforded 2.1 g of (1,1-dimethyl-2-(4-oxo-5-(4-(4-(5-methyl-[1,3,4]oxadiazol-2-yl)-3-thienyl) -benzyl)-2,3,4,5-tetrahydro-1H-naphtho[2,1-b]azepin-3-ylcarbamoyl)ethyl)carbamic acid tert-butyl ester.

¹H NMR (CDCl₃) δ 1.33 (s, 6H); 1.40 (s, 9H); 1.48–2.05 (m, 1H); 2.28 (s, 3H); 2.42 (d, 1H); 2.54 (d, 1H); 2.60–2.70 (m, 1H); 2.75–2.85 (m, 1H); 3.29 (dd, 1H); 4.46–4.54 (m, 1H); 4.88 (d, 1H); 5.30 (brs, 1H); 5.50 (d, 1H); 6.72 (brs, 1H); 7.20–7.26 (m, 5H); 7.40 (d, 1H); 7.48–7.56 (m, 2H); 7.80 (d, 1H); 7.86 (d, 1H); 7.98 (d, 1H); 8.01 (d, 1H).

To a solution of (1,1-dimethyl-2-(4-oxo-5-(4-(4-(5-methyl-[1,3,4]oxadiazol-2-yl)-3-thienyl)benzyl)-2,3,4,5-tetrahydro-1H-naphtho[2,1-b]azepin-3-ylcarbamoyl)ethyl) carbamic acid tert-butyl ester (2.1 g, 3.43 mmol) in dichloromethane (100 ml) was added trifluoroacetic acid (10 ml). The reaction mixture was stirred for 3h at ambient temperature. A 1 N sodium hydroxide solution (100 ml) was added and the phases were separated. The organic phase was treated with activated charcoal and dried (MgSO₄). The solvent was evaporated in vacuo to give 1.6 g of the title compound.

¹H NMR (CDCl₃) δ 1.22 (s, 3H); 1.25 (s, 3H); 2.10–2.18 (m, 1H); 2.26 (d, 1H); 2.29 (s, 3H); 2.32 (d, 1H); 2.60–2.75 (m, 5H); 3.27–3.33 (m, 1H); 4.53–4.60 (m, 1H); 4.90 (d, 1H); 5.47 (d, 1H); 7.20–7.25 (m, 5H); 7.43 (d, 1H); 7.49–7.56 (m, 2H); 7.79 (d, 1H); 7.85 (d, 1H); 7.98 (d, 1H); 8.00 (d, 1H); 8.40 (d, 1H).

HPLC: $R_t$=22.8 minutes (Method C)
Calculated for $C_{33}H_{33}N_5O_3S$, 1½H₂O:
C, 65.3%; H, 6.0%; N, 11.5%; Found:
C, 65.2%; H, 6.0%; N, 10.9%

EXAMPLE 3

3-((2R)-Hydroxypropylamino)-3-methyl-N-(5-(4-(4-(5-methyl-[1,3,4]oxadiazol-2-yl)thien-3-yl)benzyl)-4-oxo-2,3,4,5-tetrahydro- 1H-naphtho[2,1-b]azepin-3-yl)butyramide (2R)-(Tetrahydropyran-2-yloxy)propionaldehyde (107 mg, 0.675 mmol) was dissolved in methanol (10 ml) and added to a solution of 3-amino-3-methyl-N-(5-(4-(4-(5-methyl-[1,3,4]oxadiazol-2-yl)thien-3-yl)benzyl)-4-oxo-2,3,4,5-tetrahydro-1H-naptho[2,1-b]azepin-3-yl)butyramide (261 mg, 0.45 mmol) in methanol (10 ml) and glacial acetic acid (0.1 ml). A solution of sodium cyanoborohydride (57 mg, 0.9 mmol) in DMF (3 ml) was added and the solution was stirred for 3.5 h at room temperature. The solvent was removed in vacuo and the residue was dissolved in ethyl acetate/water (10 ml/10 ml). The phases were separated and the organic phase was dried (MgSO₄) and the solvent was removed in vacuo. The residue was dissolved in methanol (10 ml) and a 3 M solution of hydrogen chloride (1 ml, 3 mmol) in ethyl acetate was added. The solution was stirred at room temperature for 1 h and the solvent was removed in vacuo. The residue was dissolved in dichloromethane (10 ml) and washed with 1. N sodium hydroxide solution (2×10 ml). The combined aqueous layers were extracted with dichloromethane (2×10 ml). The organic layers were combined and dried (MgSO₄) and the solvent was removed in vacuo. The crude product was purified by flash chromatography on silica gel (100 ml) with dichloromethane/ethanol/ 25% aqueous ammonia (85:15:1) as eluent followed by preparative TLC (silica 20 cm×20 cm×0.2 cm, the TLC was run 3 times) with dichloromethane/ethanol/25% aqueous ammonia (85:15:1) as eluent to give 8 mg of a mixture of diastereoisomers of ³-((²R)-hydroxypropylamino)-3-methyl-N-(5-(4-(4-(5-methyl-[1,3,4]oxadiazol-2-yl)thien-3-yl)benzyl)-4-oxo-2,3,4,5-tetrahydro-1H-naphtho[2.1-b] azepin-3-yl)butyramide.

¹H NMR (CDCl₃) δ 1.10–1.40 (m, 9 H); 2.15–2.40 (m, 5H); 2.55–2.75 (m, 4 H); 3.40 (m, 1 H); 3.35 (m, 1 H); 4.10 (m, 1 H); 4.50 (m, 1 H); 4.35 and 4.45 (both d, together 1H); 5.40 and 5.50 (both d, together 1 H); 7.15–7.35 (m, 5 H); 7.40 (m, 1H); 7.45–7.60 (m, 2 H); 7.80 (dd, 1 H); 7.85 (d, 1H); 7.95 (dd, 1H); 8.05 (d, 1H); 9.10 (m, 1 H).

HPLC: $R_t$=27.8 minutes (Method B).

EXAMPLE 4

1-Aminocyclopropanecarboxylic acid (4-oxo-5-(2'-(1H-tetrazole-5-yl)-biphenyl-4-ylmethyl) -2,3,4,5-tetrahydro- 1H-naptho [2,1-b]azepin-3-yl) amide trifluoroacetate (1-(4-Oxo-2,3,4,5-tetrahydro-1H-naptho[2,1-b]azepin-3-ylcarbamoyl)cyclopropyl)carbamic acid tert-butyl ester To a solution of 1-(tert-butyloxycarbonylamino) cyclopropanecarboxylic acid (74 mg, 0.37 mmol) in DMF (6 ml) was added HOAt (50 mg, 0.37 mmol) and EDAC (71 mg, 0.37 mmol). After 10 minutes of stirring, 3-amino-4-oxo-2,3,4,5-tetrahydro-1-naphtho[2,1-]blazepine (84 mg, 0.37 mmol) and diisopropylethylamine (96 mg, 0.74 mmol) were added and the mixture was left overnight at 40° C. Water (60 ml) and ethyl acetate (60 ml) were added. The phases were separated and the organic phase was washed with 1 M HCl (60 ml), saturated NaHCO₃ (60 ml) and dried (MgSO₄). The solvent was removed in vacuo to give 148 mg of a solid. Recrystallization from a mixture of methylene chloride and ethyl acetate gave 62 mg of (1-(4-oxo-2,3,4,5-tetrahydro-1H-naptho[2, 1-b]azepin-3-ylcarbamoyl) cyclopropy)carbamic acid tert-butyl ester.

¹H-NMR (CDCl₃) δ 0.99 (s, 2H); 1.45 (m, 2H); 1.51 (s, 9H); 2.12 (m, 1H); 3.05 (m, 2H); 3.48 (m, 1H); 4.49 (m, 1H); 5.10 (brs, 1H); 7.05–8.05 (m, 8H).

(1 -(4-Oxo-(5 -(2'-(N-triphenylmethyltetrazol-5-yl) biphenyl-4-ylmethyl)-2,3,4,5-tetrahydro- 1H -naphtho[2,1-b]azepin-3-ylcarbamoyl)cyclopropyl)carbamic acid tert-butyl ester (1-(4-Oxo-2,3,4,5-tetrahydro- 1H-naptho[2, 1-b]azepin-3-ylcarbamoyl)cyclopropyl)carbamic acid tert-butyl ester (62 mg, 0.16 mmol) and dry, powdered KOH (34 mg, 0.62 mmol) were suspended in dry DMSO (2 ml) under an atmosphere of nitrogen and stirred for 10 minutes. 5-(4'-Bromomethylbiphenyl-2-yl) N-triphenylmethyltetrazole (92mg, 0.65 mmol) was added and the mixture was stirred for 30 minutes. Water (10 ml) and ethyl acetate (30 ml) were added and the phases were separated. The organic phase was dried (MgSO₄) and evaporated to a 1 ml residue which was chromatographed on Merck Silica preparative plates using heptane/ethyl acetate (1:1) as eluent. This afforded 29 mg of (1-(4-oxo-(5-(2'-(triphenylmethyltetrazol-5-yl)biphenyl-4-ylmethyl)-2,3,4,5-tetrahydro- 1H-naphtho[2,1-b]azepin-3-ylcarbamoyl)cyclopropyl)carbamic acid tert-butyl ester.
$^1$H-NMR (CDCl$_3$) δ 6 0.99 (s (br), 2H); 1.49 (s, 9H); 1.66 (s (br), 2H), 1.99 (m, 1H); 2.62 (m, 2H); 3.20 (m, 1H); 4.48 (m, 1H); 4.80 (d, 1H, J=14 Hz); 5.09 (s (br), 1H); 5.25 (d, 1H, J=14 Hz); 6.87–7.90 (m, 29 H).

A mixture of (1-(4-oxo-(5-(2'-(N-triphenylmethyl-tetrazol-5-yl)biphenyl-4-ylmethyl) -2,3,4,5-tetrahydro-1H-naphtho[2,1-b]azepin-3-ylcarbamoyl)cyclopropyl)carbamic acid tert butyl ester (29 mg) and TFA (1 ml) was stirred for 2h under an atmosphere of nitrogen. Water (1 drop) was added and the solvent was removed in vacuo. The residue was treated with methanol (0.1 ml) and diethyl ether (2 ml), filtered and washed with diethyl ether (2 ×1 ml) to afford 16 mg of 1-aminocyclopropanecarboxylic acid (4-oxo-5-(2'-(1H-tetrazole-5-yl)-biphenyl-4-ylmethyl)-2,3,4,5-tetrahydro- 1H-naptho[2,1-b]azepin-3-yl) amide trifluoroacetate.
$^1$H-NMR (CD$_3$OD) δ 6 1.30 (s, 2H); 1.65 (m, 1H); 2.15 (s, 2H); 3.38 (m, 2H); 3.45 (m, 1H); 4.35 (m, 1H), 4.92 (d, 1H, J=15 Hz); 5.35 (d, 1H, J=15 Hz), 6.98–8.15 (m, 14H).
HPLC: R$_t$=31.4 minutes (Method A).

EXAMPLE 5

3-Amino-3-methyl-N- (5-benzyl-4-oxo-2,3,4,5-tetrahydro-1H-naptho [2,1 -b]azepin-3-yl) butyramide hydrochloride
(1,1-Dimethyl-2-(4-oxo-5-benzyl-2,3,4,5-tetrahydro-1H-naphtho[2,1b ]azepin-3-ylcarbamoyl)ethyl)carbamic acid tert-butyl ester.
(1,1-Dimethyl-2-(4-oxo-2,3,4,5-tetrahydro-1H-naphtho [2,1b ]azepin-3-ylcarbamoyl)ethyl) carbamic acid tert-butyl ester (250 mg, 0.586 mmol, prepared as in example 1) was dissolved in DMSO (5 ml) and dry, powdered KOH (131 mg, 2.34 mmol) was added under an atmosphere of nitrogen and the mixture was stirred for 30 minutes. Benzyl bromide (105 mg, 0.62 mmol) was added and the mixture was stirred for 75 minutes. Water (25 ml) and ethyl acetate (25 ml) were added and the phases were separated. The organic phase was dried (MgSO$_4$) and the solvent removed in vacuo. This crude product was chromatographed on Merck Silica 60 plates using a mixture of ethyl acetate and heptane (2:1) as eluent to afford 142 mg of 1,1-dimethyl-2-(4-oxo-5-benzyl-2,3,4,5-tetrahydro-1H-naphtho[2,1b]azepine-3-ylcarbamoyl)ethyl)carbamic acid tert-butyl ester.
$^1$H NMR (CDCl$_3$) δ 1.34 (s, 6H); 1.40 (s, 9H); 1.99 (m, 1H); 2.55 (m, 1H); 2.75 (m, 1H); 3.25 (dd, 1H); 4.47 (m, 1H); 4.83 (d, 1H, J=17 Hz); 5.30 (brs, 1H); 5.45 (d, 1H, J=17 Hz); 6.71 (d, 1H, J=10 Hz); 7.21 (s, 5H), 7.25–7.98 (m, 6H).

1, 1- Dimethyl-2- (4-oxo-5-benzyl-2,3,4,5- tetrahydro-Hnaphtho[2,1]azepin-3-ylcarbamoyl)ethyl)carbamic acid tert-butyl ester (133 mg, 0.26 mmol) was dissolved in 3 M HCl in ethyl acetate (1.5 ml) and stirred overnight. Diethyl ether (5 ml) was added and the precipitated solid was filtered off and washed with diethyl ether (2×1 ml). This afforded 98 mg of 3-amino-3-methyl-N-(5-benzyl-4-oxo-2,3,4,5-tetrahydro-1H-naptho[2,1 -b]azepin-3-yl)butyramide hydrochloride.
$^1$H NMR (d$_6$-DMSO) δ 1.20 (s, 3H); 1.25 (s, 3H); 2.50–1.15 (m, 3H); 3.40 (m, 1H); 4.25 (m, 1H); 4.85 (d, 1H, J=: 17 Hz); 5.45 (d, 1H, J=17 Hz); 7.15–7.25 (m, 6H); 7.50–7.97 (m, 4H); 8.10 (d, 1H); 8.72 (d, 1H).
HPLC: R$_t$=32.7 minutes (Method A).
Calculated for C$_{26}$H$_{29}$N$_3$O$_2$, HCl, 1½ C, 65.19%; H, 6.98%; N, 8.77%; Found: C, 64.97%; H, 6.80%; N, 8.55%.

We claim:
1. A compound of the general formula I

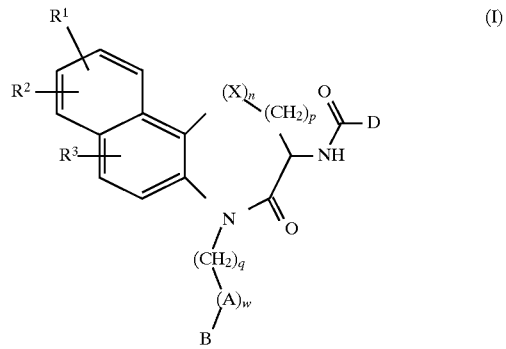

(I)

wherein
R$^1$, R$^2$ and R$^3$ are independently hydrogen, halogen, trifluoromethyl, C$_{1-6}$-alkyl, C$_{1-6}$-alkoxy or C$_{1-6}$-alkylthio;
n is 0;
p is 2;
q is 0, 1, 2, 3 or 4;
w is 0, 1 or 2;
A is

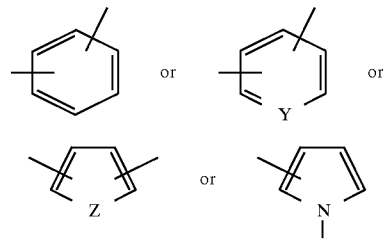

each of which may be substituted with one or more substituents selected from halogen, amino, C$_{1-6}$-alkylamino, C$_{1-6}$-alkyl, C$_{1-6}$-alkoxy or C$_{1-6}$-alkylthio; and wherein Y is =N—, and Z is —O—, —S—or >N—R$^5$, wherein R$^5$ is hydrogen or C$_{1-6}$-alkyl;

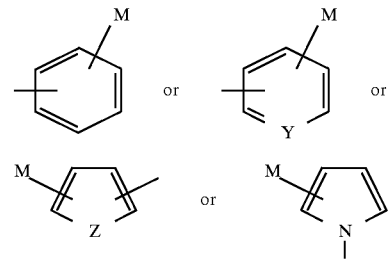

each of which may be substituted with one or more substituents selected from halogen, amino, C$_{1-6}$-alkylamino, C$_{1-6}$-alkyl, C$_{1-6}$-alkoxy or C$_{1-6}$-alkylthio; and wherein Y and Z are as defined above; M is —COOR$^{12}$, —CONR$^{12}$R$^{13}$, —NHCONR$^{12}$R$^{13}$ or —SO$_2$NR$^{12}$R$^{13}$, wherein R$^{12}$ and R$^{13}$ are independently hydrogen, C$_{1-6}$-alkyl or C$_{4-8}$-cycloalkyl, or M is any isomer of tetrazolyl, triazolyl, oxadiazolyl and thiadiazolyl which may be substituted with one or more substituents selected from halogen, amino, C$_{1-6}$-alkylamino, C$_{1-6}$-alkyl, C$_{1-6}$-alkoxy or C$_{1-6}$-alkylthio; D is

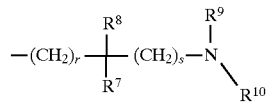

wherein r and s are independently 0, 1, 2 or 3; $R^7$ and $R^8$ are independently hydrogen or $C_{1-10}$-alkyl; or $R^7$ and $R^8$ may be joined together to form alkyl bridges wherein the bridge contains 2-6 carbon atoms; or each of $R^7$ and $R^8$ may independently be joined to one or both of $R^9$ and $R^{10}$ to form alkyl bridges wherein the bridge contains 2–5 carbon atoms; $R^9$ and $R^{10}$ are independently hydrogen, phenyl, substituted phenyl, branched or unbranched $C_{1-10}$-alkyl or branched or unbranched $C_{1-10}$-hydroxylalkyl; or a pharmaceutically acceptable salt thereof.

2. A compound according to claim 1, wherein w is 1.

3. A compound according to claim 1, wherein $R^1$, $R^2$ and $R^3$ represent hydrogen.

4. A compound according to claim 1, wherein q is 1, and

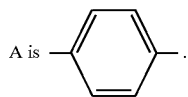

5. A compound according to claim 1, wherein B is

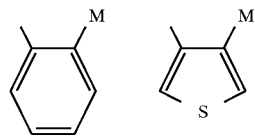

M is selected from the group consisting of unsubstituted tetrazolyl and oxadiazolyl substituted with methyl.

6. A compound according to claim 5, wherein the oxadiazole is 1,3,4-oxadiazole.

7. A compound according to claim 1, wherein r is 1, s is 0, $R^7$ and $R^8$ each represent $C_{1-6}$-alkyl, and $R^9$ and $R^{10}$ each represent hydrogen or one of $R^9$ and $R^{10}$ is $C_2$-hydroxyalkyl and the other is hydrogen.

8. A compound according to claim 7, wherein $R^7$ and $R^8$ each represent methyl.

9. A compound selected from the group consisting of:

3-Amino-3-methyl-N-(4-oxo-5-(2'-(tetrazol-5-yl)biphenyl-4-ylmethyl)-2,3,4,5tetrahydro-1H-naphtho[2,1-b]azepin-3-yl)butyramide;

3-Amino-3-methyl-N-(4-oxo-5-(4-(4-(5-methyl-[1,3,4]oxadiazol-2-yl)-thien-3-yl)benzyl)-2,3,4,5-tetrahydro-1H-naphtho-[2,1-b]azepin-3-yl)butyramide;

3-((2R)-Hydroxypropylamino)-3-methyl-N-(5-(4-(4-(5-methyl-[1,3,4]oxadiazol-2-yl)thien-3-yl)benzyl)-4-oxo-2,3,4,5-tetrahydro-1H-naphtho [2,1 -b]azepin-3-yl)butyramide;

1-Aminocyclopropanecarboxylic acid (4-oxo-5-(2'-(1H-tetrazole-5-yl)-biphenyl-4-ylmethyl)-2,3,4,5-tetrahydro- 1H-naptho[2,1-b]azepin-3-yl) amide; and 3-Amino-3-methyl-N-(5-benzyl-4-oxo-2,3,4,5-tetrahydro-1H-naptho[2,1-b]azepin-3-yl)butyramide.

10. A pharmaceutical composition comprising, as an active ingredient, a compound according to claim 1 together with a pharmaceutically acceptable carrier or diluent.

11. A composition according to claim 10 in unit dosage form comprising from about 0.0001 to about 500 mg of the compound according to any one of claims 1 through 10 or a pharmaceutically acceptable salt thereof.

12. A pharmaceutical composition according to claim 10, for oral, transdermal, pulmonary, or parenteral administration.

13. A method of stimulating the release of growth hormone from the pituitary, the method comprising administering to a subject in need thereof an effective amount of a compound according to claim 1.

14. A method according to claim 13, wherein the effective amount of the compound is in the range of from about 0.0001 to about 100 mg/kg body weight per day.

15. A method for making a preparation useful in the treatment of ailments or disorders resulting from a deficiency in growth hormone comprising admixing an effective amount of a compound according to claim 1 with a suitable carrier and/or diluent and formulating the admixture for oral, nasal, or transdermal administration, injection or infusion.

* * * * *

UNITED STATES PATENT AND TRADEMARK OFFICE
CERTIFICATE OF CORRECTION

Page 1 of 2

PATENT NO. : 5,817,654
DATED : October 6, 1998
INVENTOR(S) : Thogersen et al.

It is certified that error appears in the above-identified patent and that said Letters Patent is hereby corrected as shown below:

Col. 6, line 8: delete "glutamire" and insert --glutamine--

Col. 8, line 66: delete "6" before 3.36

Col. 10, line 10: delete "Dirnethyl" and insert --Dimethyl--

Col. 10, line 66: delete "maimer" and insert --manner--

Col. 14, line 17: delete "$^3$-(($^2$R" and insert --3-((2R--

Col. 15, line 6: delete "6" before 0.99

Col. 15, line 22: delete "6" before 1.30

Col. 15, lines 54: delete "Hnaphtho[2,1]" and insert --1Hnaphtho[2,1b]--

UNITED STATES PATENT AND TRADEMARK OFFICE
CERTIFICATE OF CORRECTION

PATENT NO. : 5,817,654
DATED : October 6, 1998
INVENTOR(S) : Thogersen et al.

It is certified that error appears in the above-identified patent and that said Letters Patent is hereby corrected as shown below:

Col. 15, line 67: insert --$H_2O$:-- after "1½"

Col. 16, line 44, claim 1: insert --B is hydrogen or-- after "-alkyl;"

Signed and Sealed this

Twenty-second Day of June, 1999

Q. TODD DICKINSON

*Attest:*

*Attesting Officer*            Acting Commissioner of Patents and Trademarks